United States Patent [19]

Munson, Jr.

[11] 4,296,092

[45] Oct. 20, 1981

[54] MUCOLYTIC BENZENE AND THIOPHENE-CARBOTHIOIC ACID 2-AMINOALKYL ESTER ACID SALTS

[75] Inventor: Harry R. Munson, Jr., Richmond, Va.

[73] Assignee: A. H. Robins Company, Inc., Richmond, Va.

[21] Appl. No.: 95,761

[22] Filed: Nov. 19, 1979

Related U.S. Application Data

[63] Continuation-in-part of Ser. No. 932,747, Aug. 10, 1978, abandoned.

[51] Int. Cl.³ .................. A61K 9/00; A61K 31/38; A61K 31/265
[52] U.S. Cl. .................. 424/43; 424/45; 424/46; 424/275; 424/301; 549/72
[58] Field of Search .................. 424/301, 275, 43, 45; 549/72; 260/455 R

[56] References Cited

PUBLICATIONS

Foye et al., J. Pharm. Sci., vol. 51, No. 2, Feb. 1962, pp. 168–171.
Sheffner, Arn. N.Y. Acad. Sci. 106, 298–310 (1943).

*Primary Examiner*—Leonard Schenkman

[57] ABSTRACT

Benzene and 2-thiophene carbothioic and 2-aminoalkyl ester acid salts having the formula:

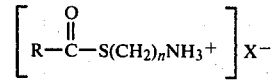

wherein R is 2-thiophene, benzene or substituted benzene; n is 2 and 3 and $X^-$ is a chlorine or bromine radical and methods of using the compounds and compositions are disclosed.

18 Claims, No Drawings

MUCOLYTIC BENZENE AND THIOPHENE-CARBOTHIOIC ACID 2-AMINOALKYL ESTER ACID SALTS

The present invention is a continuation-in-part application of copending application Ser. No. 932,747 filed Aug. 10, 1978 now abandoned.

BACKGROUND OF THE INVENTION

1. Field of Invention

The present invention is concerned with certain carbothioic acid-2-aminoalkylesters possessing mucolytic activity and is particularly concerned with benzene and substituted benzene and 2-thiophene-carbothioic acid-2-aminoalkylester acid salts in combatting and controlling mucus build-up in an animal exhibiting lung congestion and compositions for use as mucolytic agents.

2. Description of the Prior Art

The prior art discloses synthesis of benzene carbothioic acid-2-aminoethylester hydrochloride, W. O. Foye et al, J. Pharm. Sci. 51 (2), 168–71 (1962) but there is no disclosure of mucolytic activity. Substitution on benzene has not been disclosed. The prior art discloses certain mucolytic agents such as N-acetyl-cysteine having a free sulfhydryl group, which group compounds of the present invention do not have. A. L. Sheffner, Ann. N.Y. Acad. Sci. 106, 298–310 (1963) established the use of gastric mucin mucoprotein as a test media in development of N-acetyl-L-cysteine as a mucolytic agent in the treatment of lung disease. A recent publication: "Pharmacokinetics of Oral Acetylcysteine" by Rodenstein, D., et al. describes effectiveness of orally administered acetylcysteine as a mucolytic agent in *Clinical Pharmacokinetics* 3: 247–254 (1978) ADIS PRESS 1978.

SUMMARY OF THE INVENTION

The compounds of the present invention are benzene-substituted benzene and 2-thiophenecarbothioic acid-2-aminoalkylester acid salts illustrated generally by the following formula:

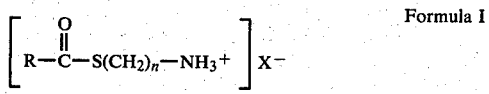

Formula I wherein;

R is 2-thiophene, benzene or benzene substituted by one to three radicals which are selected from halogen lower-alkyl, lower-alkoxy, carboxy or trifluoromethyl and may be the same or different and in various positions relative to one another on the ring.

$X^-$ is a chlorine or bromine radical and n is 2 or 3.

The compounds have mucolytic activity and are useful in dissolving and diluting mucus in warm-blooded animals exhibiting or suffering from lung congestion.

The compounds act to dilute mucus when administered by topical application as by inhalation and systemically from lung tissue surface when administered internally such as orally.

DESCRIPTION OF THE PREFERRED EMBODIMENTS

The compounds described hereinafter and represented by the foregoing Formula I have been shown by a modification of the method of S. J. Carne et al., J. Phys. 242, 116 (1974) as described hereinbelow shown to have mucolytic activity in animals.

Compounds for which mucolytic activity was found to be of the same order of magnitude as N-acetyl-L-cysteine on rat stomach mucus are the preferred compounds which are:

(1) Benzenecarbothioic acid, 2-aminoethyl ester, monohydrochloride, (2) 4-Chlorobenzenecarbothioic acid, 2-aminoethyl ester, monohydrochloride, (3) 4-Methylbenzenecarbothioic acid, 2-aminoethyl ester, monohydrochloride, (4) 4-Methoxybenzenecarbothioic acid, 2-aminoethyl ester, monohydrochloride, (5) 2-Thiophenecarbothioic acid, 2-aminoethyl ester, monohydrochloride.

The method used to establish mucolytic activity in compounds of the present invention is as follows.

Female Sprague-Dawley (Charles River Labs) 120–180 g rats are fasted 16 hours on wire, housed two animals per cage. To minimize coprophogia, the lights are left on during the fast. Two cc of water are given orally to each rat to minimize internal debris. Thirty minutes later the rats are sacrificed by cervical dislocation. The stomachs are removed, trimmed of excess tissue and the epithelial portion discarded. The glandular portion is cut sufficiently along the greater and lesser curvature to cause eversion of the stomach before placing it in the drug solution. Stomachs with a fecal odor or containing visible fecal matter are discarded. Stomachs are placed in 10 cc of solution (water or 50% PEG 300-$H_2O$ depending on solubility) containing 2.5 mg test compound/ml for 40 minutes. After drug treatment stomachs are placed in 10 cc Alcian blue solution (Solution 1) for 90 minutes where the dye complexes with the stomach mucus. After two successive 10-minute washes in 10 cc of 0.25 M sucrose solution (Solution 2), the stomachs are placed in 10 cc 0.5 $MgCl_2$ solution (Solution 3) for one hour to remove the complexed dye. The $MgCl_2$ supernatant is shaken with 10 cc diethyl ether in a 60 cc separatory funnel to remove lipids. The aqueous phase is drained into a Spectronic 20 tube and the percent transmission is read at 605 m$\mu$ in a Spectronic 20 spectrophotometer. The percent transmission is converted to $\mu g/ml$ of Alcian Blue from a standard curve. (P. Whiteman, Biochem. J. 131, 351–57 (1973). Each drug or drug vehicle (control) is tested on three stomachs. Mean differences between treated and control values are expressed as percentages.

Solution 1-Alcian Blue, 0.05% w/v (1 liter)

54.8 g. sucrose (0.15 M)
6.8 g. sodium acetate
900 cc. deionized water

Dissolve with a magnetic stirrer and adjust to pH 5.8. Add 500 mg. Alcian Blue 8 GN (Matheson Coleman & Bell #8E13). Fill to one liter in a volumetric flask. Refrigerate. Use only for one week.

Solution 2-Sucrose, 0.25 M (1 liter)

Add 85.6 g of sucrose to one liter volumetric flask. Fill to volume with deionized water. Use only for one week.

Solution 3-Magnesium Chloride, 0.5 M (1 liter)

Add 101.7 g Mg $Cl_2.6H_2O$ A.C.S. to a one liter volumetric flask. Fill to volume with deionized water.

It is therefore an object of the present invention to provide certain novel carbothioic acid, 2-aminoalkylester acid salts having mucolytic activity in a warm-blooded animal.

A further object is to provide a method of using benzene and substituted benzene and 2-thiophene carbothioic acid-2-aminoalkylester acid salts as mucolytic agents to combat mucus build-up in a warm-blooded animal suffering from lung congestion.

A still further object is to provide pharmaceutical compositions containing the compounds useful for controlling congestion due to mucus in a warm-blooded animal body.

Additional objects and advantages of the present invention will be apparent to one skilled in the art and still others will become apparent from the following description of the best mode of carrying out the present invention and from the appended claims.

In the definition of the symbols and in Formula I given above, and where they appear elsewhere throughout the claims and specifications hereof, the terms have the following significance.

"Benzene substituted by one to 3 radicals" as used herein shall mean a phenyl radical which is substituted by one to 3 radicals selected from the group as hereinabove defined under the definition of R and these substituents can be in various available positions of the phenyl nucleus and when more than one substituent is present, may be the same or different and may be in various position combinations relative to each other. The lower-alkyl and lower-alkoxy substituents each have preferably from one to four carbon atoms which can be arranged as straight or branched chains. Examples of the preferred substituents are methyl, ethyl, propyl, butyl, fluoro, bromo, chloro, iodo, methoxy, ethoxy, butoxy, carboxy and trifluoromethyl radicals.

METHOD OF PREPARATION

The benzene and substituted benzene and thiophenecarbothioic acid, 2-aminoalkylester acid salts are prepared by procedures known for preparing the benzene derivatives as represented by the following equation:

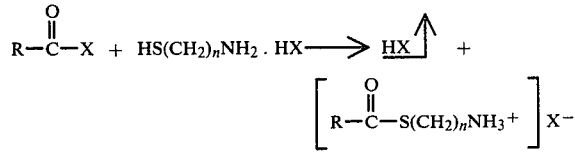

wherein R, n and $X^-$ are as defined hereinabove.

Generally, the reactants are mixed and heated over a steam jet until a mass of crystals are formed. The mass of crystals is then broken up, triturated with ligroine and recrystallized from anhydrous ethanol.

The following examples of preparation of compounds are only intended to illustrate the present invention and are not to be construed as limiting the invention in any respect.

EXAMPLE 1

Benzenecarbothioic Acid, 2-Aminoethylester, Monohydrochloride

A mixture of benzoyl chloride, 15 ml. (ca 0.13 mole) and 2-aminoethanethiol hydrochloride, 4.54 g. (0.04 mole) was heated (protected from moisture) over a steam jet for 2 hours. Slight cooling produced a mass of crystals. After trituration with 60°–110° C. ligroine filtration and drying, the crystals melted at 177°–180° C. Several recrystallizations from anhydrous ethanol produced a colorless solid which melted at 178.5°–179.5° C. Nuclear Magnetic Resonance (NMR), Mass Spectrophotometer (MS) and Infra Red (IR) analysis all supported structure of the title compound in accordance with Formula I. Yield was 5.1 g. (59.1%).

Analysis: Calculated for $C_9H_{12}ClNOS$: C,49.65; H,5.55; N,6.43; Found: C,49.58; H,5.59; N,6.49.

EXAMPLE 2

4-Chlorobenzenecarbothioic Acid, 2-Aminoethyl Ester, Monohydrochloride

A mixture of freshly distilled p-chlorobenzoyl chloride, 60 ml. (0.47 mole) and 2-aminoethanethiol hydrochloride, 18.18 g. (0.16 mole) was heated (protected from moisture) over a steam jet for 2 hours. A solid crystalline mass formed as the reaction went to completion. After careful trituration with warm 60°–110° C. ligroine, crystals were separated by filtration while washing with ligroine. After two recrystallizations from anhydrous ethanol, the product, 39.0 g. (96.5%), melted at 208°–209.5° C. NMR, MS and IR analyses all supported structure of the title compound in accordance with Formula I.

Analysis: Calculated for $C_9H_{11}Cl_2SNO$: C,42.87; H,4.40; N,5.55; Found: C,42.79; H,4.43; N,5.59.

EXAMPLE 3

4-Methylbenzenecarbothioic Acid, 2-Aminoethyl Ester, Monohydrochloride

A mixture of freshly distilled p-toluoyl chloride, b.p. 122° C./32 mm, Hg., 30 ml. (ca 0.18 moles) and 2-aminoethanethiol hydrochloride, 9.68 g. (0.085 moles) was heated (protected from moisture) over a steam jet for 2.25 hours. A solid crystalline mass formed on completion of the reaction. The mass was crushed and carefully triturated with warm 60°–110° C. ligroine and crystals were separated by filtration and washed with warm ligroine. After two recrystallizations from anhydrous ethanol, the product, 19.07 g. (97%), melted at 206.5°–208° C. NMR, MS and IR analyses all supported the structure of the title compound in accordance with Formula I.

Analysis: Calculated for $C_{10}H_{14}NOClS$: C,51.83; H,6.09; N,6.04; Found: C,51.57; H,6.06; N,6.11.

EXAMPLE 4

4-Methoxybenzenecarbothioic Acid, 2-Aminoethyl Ester, Monohydrochloride

A mixture of p-anisoyl chloride, 23 ml. (ca 0.135 mole) and 2-aminoethanethiol hydrochloride, 7.4 g. (0.065 mole) was heated (protected from moisture) over a steam jet for about 2 hours. The resultant crystalline mass was crushed and carefully triturated with warm 60°–110° C. ligroine and crystals were separated by filtration and washed with warm ligroine. After two recrystallizations from anhydrous ethanol, the product, 14.6 g. (90.6%) melted at 191.5°–193° C. NMR, MS and IR analyses all supported the structure of the title compound in accordance with Formula I.

Analysis: Calculated for $C_{10}H_{14}ClNO_2S$: C,48.48; H,5.69; N,5.65; Found: C,48.42; H,5.73; N,5.66.

EXAMPLE 5

When in the procedure of Example 1, benzoyl chloride is replaced by equal molar amounts of
3,4,5-trimethoxybenzoyl chloride,
4-fluorobenzoyl chloride,
3-trifluoromethylbenzoyl chloride,
3,4-dichlorobenzoyl chloride,
3,4-dimethylbenzoyl chloride, and
4-carboxybenzoyl chloride
there are obtained
3,4,5-trimethoxybenzenecarbothioic acid, 2-aminoethyl ester hydrochloride,
4-fluorobenzenecarbothioic acid, 2-aminoethyl ester hydrochloride,
3-trifluoromethylbenzenecarbothioic acid, 2-aminoethyl ester hydrochloride,
3,4-dichlorobenzenecarbothioic acid, 2-aminoethyl ester hydrochloride,
3,4-dimethylbenzenecarbothioic acid, 2-aminoethyl ester hydrochloride, and
4-carboxybenzenecarbothioic acid, 2-aminoethyl ester hydrochloride.

EXAMPLE 6

When in the procedure of Example 1, 2-aminoethanethiol hydrochloride is replaced by equal molar amounts of 3-aminopropanethiol hydrochloride, there is obtained
benzenecarbothioic acid-3-aminopropylester hydrochloride.

EXAMPLE 7

When in the procedure of Example 1, 2-aminoethanethiol hydrochloride is replaced by equal molar amounts of 3-aminopropanethiol hydrochloride and benzoyl chloride is replaced by
p-chlorobenzoyl chloride,
p-toluoyl chloride, or
p-anisoyl chloride
there are obtained
4-chlorobenzenecarbothioic acid, 3-aminopropyl ester hydrochloride,
4-methylbenzenecarbothioic acid, 3-aminopropyl ester hydrochloride, and
4-methoxybenzenecarbothioic acid, 3-aminopropyl ester hydrochloride.

EXAMPLE 8

2-Thiophenecarbothioic Acid, 2-Aminoethyl Ester, Hydrochloride

A mixture of freshly distilled 2-thiophenecarbonyl chloride, 15.8 g. (0.108 mole) and 2-aminoethanethiol hydrochloride, 11.3 g. (0.1 mole) was heated (protected from moisture) over a steam jet for 6 hours. The resulting solid crystalline mass was crused and triturated with warm 60°–110° C. ligroine and filtered to collect the crystals. After two recrystallizations from anhydrous ethanol, the product, 8.41 g. (75.5%) melted at 195°–196.5° C. NMR, MS and IR all supported the structure of the title compound in accordance with Formula I.

Analysis: Calculated for $C_7H_{10}ClNOS_2$: C,37.58; H,4.51; N,6.26; Found: C,37.68; H,4.50; N,6.30.

EXAMPLE 9

When in the procedure of Example 8, 2-aminoethanethiol hydrochloride is replaced by equal molar amounts of 3-amino propanethiol hydrochloride, there is obtained thiophenecarbothioic acid, 3-aminopropyl ester hydrochloride.

The pharmaceutical compositions of this invention comprise compounds of Formula I above in an amount sufficient to provide effective action against lung congestion in warm-blooded animal subjects when applied topically as an inhalant.

The compounds of Formula I are administered in an amount sufficient to induce liquefaction of mucus in the respiratory tract of warm-blooded animals in need thereof. Intratracheal administration of the compounds of Formula I is effected by various inhalation or instillation means such as nose drops, sprays, aerosols and the like. Another suitable means of administration is by insufflation of micronized particle or ultra-fine powder utilizing only the energy of the inspiratory action or by use of aerosol propellants. Solutions or suspensions having about 0.5 to 5% weight of the mucolytic agent of Formula I are suitable for application by spraying with an atomizer, nebulizer, aerosol and the like.

Oral administration of the compounds of Formula I is also contemplated which dosage may take form of capsules, tablets, suspensions, syrups and the like.

It will be readily apparent to those skilled in the medical art that the correct dosage of a compound to be employed with any particular mammalian subject is determined by the severity of the condition requiring mucolytic therapy, as well as the age, sex, weight and general physical condition of the subject. Individual doses ranging from 5–100 mg. for inhalation by man are suitable and may be required for the mucolytic effect. Somewhat higher dosages are required for oral administration ranging from 50–200 mg or possibly higher depending on the severity of the infection and size of the host.

The pharmaceutical compositions may take the form of dilutions of the micronized compounds in dusts or solutions and suspensions in liquids suitably dispensed for inhalation as illustrated following.

| A. Powder for Administration via Inhaler Device. | |
| --- | --- |
| 4-Chlorobenzenecarbothioic acid, 2-aminoethyl ester monohydrochloride of Example 2, micronizecd | 2.5 g. |
| Lactose Powder | 2.5 g. |

The powders are blended aseptically and filled into hard gelatin capsules each containing 50 mg of the mixture. This is suitable for dispersion into the inspired breath by means of a breath-operated inhaler device containing means for rupture of the capsule wall prior to dosing.

| B. Sterile Solution for Administration via Inhaler Device. | |
| --- | --- |
| 1. Active ingredients | 100 mg. |
| 2. Alcohol 95%, q.s. | 1.0 cc. |

Dissolve No. 1 and 2 by warming and administer by means of breath-operated inhaler device.

| C. Aqueous Solution. | |
| --- | --- |
| 1. Active ingredient, Ex. 1, 3 or 5 | 10 g. |
| 2. Distilled water | 90 |

| C. Aqueous Solution. | |
| --- | --- |
| | Total 100 g. |

Dissolve 1 in 2 and dilute to dosage forms and administer by means of inhaler device or aerosol.

| D. Capsules. | |
| --- | --- |
| 1. Active ingredient | 100 mg. |
| 2. Lactose | 200 |

Mix and fill gelatin capsule.

What is claimed is:

1. A method of combatting mucus build-up in an animal body for the purpose of alleviating lung congestion in an animal suffering therefrom which comprises administering to said animal an effective amount of a compound having the formula:

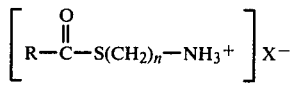

wherein;
R is 2-thiophene, benzene and benzene substituted by one to 3 radicals which may be the same or different, selected from halogen, lower-alkyl, lower-alkoxy, carboxy, trifluoromethyl;
$X^-$ is a chlorine or bromine radical, and
n is 2 or 3.

2. The method of claim 1 wherein the compound is benzenecarbothioic acid, 2-aminoethyl ester, monohydrochloride.

3. The method of claim 1 wherein the compound is 4-chlorobenzenecarbothioic acid, 2-aminoethyl ester, monohydrochloride.

4. The method of claim 1 wherein the compound is 4-methylbenzenecarbothioic acid, 2-aminoethyl ester, monohydrochloride.

5. The method of claim 1 wherein the compound is 4-methoxybenzenecarbothioic acid, 2-aminoethyl ester, monohydrochloride.

6. The method of claim 1 wherein the compound is thiophenecarbothioic acid, 2-aminoethyl ester, monohydrochloride.

7. A method of combatting mucus build-up in an animal body for the purpose of alleviating lung congestion in an animal suffering therefrom by administering via inhalation an amount of a compound effective for dissolving the mucus causing the congestion having the formula:

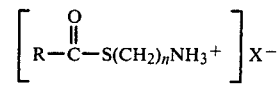

wherein;
R is 2-thiophene, benzene and benzene substituted by one to 3 radicals which may be the same or different, selected from halogen, lower-alkyl, lower-alkoxy, carboxy, trifluoromethyl;
$X^-$ is a chlorine or bromine radical, and
n is 2 or 3.

8. The method of claim 7 wherein the compound is benzenecarbothioic acid, 2-aminoethyl ester, monohydrochloride.

9. The method of claim 7 wherein the compound is 4-chlorobenzenecarbothioic acid, 2-aminoethyl ester, monohydrochloride.

10. The method of claim 7 wherein the compound is 4-methylbenzenecarbothioic acid, 2-aminoethyl ester, monohydrochloride.

11. The method of claim 7 wherein the compound is 4-methoxybenzenecarbothioic acid, 2-aminoethyl ester, monohydrochloride.

12. The method of claim 7 wherein the compound is 2-thiophenecarbothioic acid, 2-aminoethyl ester, monohydrochloride.

13. A pharmaceutical composition useful for inhalation as a mucolytic agent in an animal body suffering from lung congestion comprised of (a) 0.5 to 5 weight % of a compound of the formula:

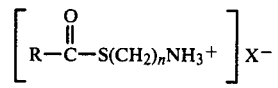

wherein;
R is 2-thiophene, benzene and benzene substituted by one to 3 radicals selected from halogen, lower alkyl, lower alkoxy, carboxy or trifluoromethyl,
$X^-$ is a chlorine or bromine radical, and
n is 2 or 3, and
(b) a pharmaceutically acceptable liquid carrier, together with an aerosol propellant therefor.

14. The composition of claim 13 wherein the compound is 4-chlorobenzenecarbothioic acid, 2-aminoethyl ester monohydrochloride.

15. The composition of claim 13 wherein the compound is 4-methylbenzenecarbothioic acid, 2-aminoethyl ester monohydrochloride.

16. The composition of claim 13 wherein the compound is 4-methoxybenzenecarbothioic acid, 2-aminoethyl ester monohydrochloride.

17. The composition of claim 13 wherein the compound is 2-thiophenecarbothioic acid, 2-aminoethyl ester monohydrochloride.

18. 2-thiophenecarbothioic acid, 2-aminoethyl ester monohydrochloride.

* * * * *